United States Patent [19]
Wirth et al.

[11] 3,965,126
[45] June 22, 1976

[54] RECOVERING MALEIC ANHYDRIDE FROM THE EFFLUENT FROM THE PRODUCTION OF PHTHALIC ANHYDRIDE

[75] Inventors: Friedrich Wirth; Erich Renauer, both of Ludwigshafen; Hans Von Ammon, Gruenstadt; Curt Schneider, Kirchheim; Hubert Suter, Ludwigshafen, all of Germany

[73] Assignee: BASF Aktiengesellschaft, Ludwigshafen (Rhine), Germany

[22] Filed: Oct. 25, 1974

[21] Appl. No.: 517,887

[30] Foreign Application Priority Data
Nov. 9, 1973 Germany............................ 2356049

[52] U.S. Cl. .......................... 260/346.8 M; 159/49
[51] Int. Cl.$^2$..................... B01D 1/22; B01D 1/26; C07C 57/14
[58] Field of Search ................ 159/49; 260/346.8 M

[56] References Cited
UNITED STATES PATENTS

| | | | |
|---|---|---|---|
| 2,683,110 | 7/1954 | Rousseau ................ | 260/346.8 M X |
| 2,688,622 | 9/1954 | Jaquay ........................ | 260/346.8 M |
| 2,696,489 | 12/1954 | Adams et al. ................ | 260/346.8 M |
| 3,261,847 | 7/1966 | Sullivan ........................ | 260/346.8 M |

FOREIGN PATENTS OR APPLICATIONS

| | | | |
|---|---|---|---|
| 1,928,207 | 12/1970 | Germany ..................... | 260/346.8 M |

OTHER PUBLICATIONS
Kirk–Othmer, Encyclopedia of Chemical Technology, Sec. Edition vol. 12, p. 829.

*Primary Examiner*—Morris O. Wolk
*Assistant Examiner*—Michael S. Marcus
*Attorney, Agent, or Firm*—Johnston, Keil, Thompson & Shurtleff

[57] ABSTRACT

Maleic anhydride is recovered by evaporating the effluent from the production of phthalic anhydride at from 40° to 150°C and from 50 to 760 mm to a water content of less than 10% by weight, heating the concentrate in a thin-film or falling-film evaporator at from 100 to 600 mm at from 120° to 180°C and distilling it in a column. The pure maleic anhydride is withdrawn laterally and the aqueous condensate is recycled to the offgas scrubber.

7 Claims, No Drawings

RECOVERING MALEIC ANHYDRIDE FROM THE EFFLUENT FROM THE PRODUCTION OF PHTHALIC ANHYDRIDE

This application discloses and claims subject matter described in German Patent Application P 23 56 049.8, filed Nov. 9, 1973, which is incorporated herein by reference.

This invention relates to a process for the recovery of maleic anhydride from an aqueous wash solution which has been obtained in the scrubbing with water of the offgas obtained in the production of phthalic anhydride by catalytic oxidation of o-xylene with air.

Phthalic anhydride is manufactured on an industrial scale by catalytic air oxidation of p-xylene or naphthalene. In this process the phthalic anhydride is separated in condensers by cooling the reaction gas. The offgas is usually subjected to scrubbing after the separation process, i.e., the offgas is treated for example at a temperature of from 25° to 60°C with water so that a wash solution is formed which, in addition to residues of phthalic acid, contains oxidation products of o-xylene such as maleic acid, benzoic acid, citraconic acid, toluic acid, tolualdehyde and phenols.

This liquor has already been made use of for the production of fumaric acid. Industrial methods of processing the liquor into maleic anhydride have however not been developed because of the difficulty in separating maleic anhydride in the necessary high purity.

We have now found that maleic anhydride can be recovered advantageously from effluents from the production of phthalic anhydride by evaporating an aqueous solution (which has been obtained in the production of phthalic anhydride by catalytic oxidation of o-xylene with air by scrubbing the offgas obtained with water and which contains up to 40% by weight of maleic acid in addition to other oxidation products) in one or more stages at temperatures of from 40° to 150°C and pressures of from 50 to 760 mm to a water content of less than 10% by weight, heating the concentrate in an agitated thin-film or falling-film evaporator at a pressure of from 100 to 600 mm at temperatures of from 120° to 180°C, distilling the product obtained by this evaporation, and cooling to 110° to 140°C in a column so that volatiles are taken overhead and the pure maleic anhydride is removed in a lateral outlet, the whole of the aqueous condensate obtained by evaporation of the aqueous solution and dehydration being returned to the offgas scrubber.

The aqueous solutions which are suitable for the new process and which are obtained by offgas scrubbing in the said phthalic anhydride manufacture contain for example, in addition to from 10 to 30% by weight of maleic acid, from 1 to 3% by weight of phthalic acid, from 1 to 1.5% by weight of benzoic acid, from 1 to 2.5% by weight of citraconic acid and from 10 to 100 ppm of other oxidation products of o-xylene such as toluic acid, tolualdehyde and phenols.

In accordance with the process of the invention the wash solution is concentrated to a water content of less than 10% by weight in one or more stages at temperatures of from 40° to 150°C and preferably at from 60° to 140°C and a pressure of from 50 to 760 mm and preferably from 100 to 600 mm. It is advantageous to carry out the concentration in a falling-film or thin-film evaporator, for example by first concentrating the solution in a falling-film evaporator at a temperature of from 80° to 110°C and a pressure of from 400 to 760 mm to a water content of from 30 to 60% by weight and then further concentrating this concentrated solution in a second falling-film evaporator or in a thin-film evaporator at a temperature of from 80° to 120°C and a pressure of from 300 to 600 mm to a water content of less than 10% by weight. The wash solution may however be concentrated to a water content of less than 10% by weight in only one film evaporator.

The concentrate thus obtained is then heated in a thin-film or falling-film evaporator at a pressure of from 100 to 600 mm and preferably at from 150 to 250 mm at a temperature of from 120° to 180°C and preferably from 125° to 160°C and the crude maleic anhydride obtained by evaporation and cooling to from 110° to 140°C and preferably from 120° to 130°C is supplied to a column in which the volatiles are taken overhead and the pure maleic anhydride is withdrawn laterally. For example use may be made of a column having 35 trays which is operated at a pressure of from 50 to 200 mm, a bottoms temperature of from 140° to 170°C and a head temperature of from 115° to 170°C.

According to an advantageous procedure the vapor mixture obtainable by evaporation of the concentrate in the falling-film or thin-film evaporator is passed through three successive condensers having different stages of cooling of which the first is kept at from 120° to 125°C, the second at 75° to 80°C and the third at ambient temperature. The condensate obtained in the first condenser is supplied direct to the column distillation and the condensate obtained in the second condenser is supplied to the final thin-film or falling-film evaporator, while the remaining condensate is returned to the offgas scrubber.

Non-volatile or heavy impurities are removed in the process according to the invention with the residue of the thin-film or falling-film evaporator of the final dehydration stage. For smooth operation of the continuously operated plant the concentration of maleic acid in this residue is kept at from 30 to 70% by weight to avoid stoppages in the pipelines.

Maleic anhydride is obtained according to the new process in a yield of from 82 to 86% by weight based on maleic acid contained in the wash water. The loss of about 15% by weight is due to the high proportion of byproducts in the offgas from the manufacture of phthalic anhydride and to the formation of fumaric acid. Although the process of the invention aims at avoiding the formation of fumaric acid, it is impossible to prevent such formation completely. The amounts of fumaric acid formed are from about 1 to 3% by weight based on the maleic acid present. The fumaric acid is discharged, as already stated, with the residue of the thin-film evaporator of the final evaporation stage in which the concentration of maleic anhydride is kept at from 30 to 70% by weight. This residue can be disposed of by burning.

According to the new process there is surprisingly obtained a pure maleic anhydride which after having been heated for a period of three hours at 160°C has a color number of 40 hazes (APHA) and a melting point of 52.6°C. The product thus satisfies the purity requirements for all the usual applications. This result could not have been expected having regard to the known deleterious effect on the quality of the maleic anhydride and particularly its heat resistance of the other oxidation products contained in the effluents from phthalic anhydride manufacture.

Another significant advantage of the process according to the invention is that the whole of the aqueous condensate obtained by evaporation of the aqueous solution can be returned to the scrubber used for treating the offgas obtained in the phthalic anhydride manufacture. The incidence of contaminated effluent from the manufacture of phthalic anhydride and from the recovery of maleic anhydride is thus completely avoided.

The fact that the process of the invention can be carried out so advantageously with the complete reuse of the aqueous condensate is very surprising because it would have been expected that this procedure would lead to an accumulation of byproducts such as aldehydes and phenols and therefore to impairment of the quality of the maleic anhydride recovered.

The following Example illustrates the invention.

EXAMPLE 3200 parts of a 22% solution of maleic acid which contains 4% of other acids such as phthalic acid, citraconic acid and benzoic acid is supplied per hour through a tubular heater which preheats to 100°C to a falling-film evaporator. This solution has been obtained by scrubbing offgas obtained in the manufacture of phthalic anhydride by catalytic oxidation of o-xylene with air at a temperature of 40°C. In the first evaporator the solution is concentrated at atmospheric pressure and at 120°C to a content of 40% of maleic acid. The aqueous condensate is returned to the offgas scrubber.

In the second stage the solution obtained is evaporated in a thin-film evaporator at a pressure of 300 mm and a temperature of 140°C to a water content of 4%. The temperature is maintained in the evaporator by heating the wall of the evaporator with steam at 12 bar. The aqueous condensate is returned to the offgas scrubber.

The melt thus obtained is immediately supplied to a thin-film evaporator in which it is heated to 160°C at 250 mm. The temperature is maintained by heating the wall of the evaporator with a heating medium at 220°C. The remainder of the water is thus evaporated and moreover water is eliminated from maleic acid with the formation of maleic anhydride. At the same time such an amount of maleic anhydride formed is evaporated that a melt can be discharged which contains 40% of maleic anhydride. Of the 830 parts of acids introduced, 112 parts of acid and anhydride are separated together with 74 parts of maleic anhydride as a residue. The aqueous condensate is returned to the offgas scrubber.

The vapors leaving the evaporator are partly condensed by passage through three successive condensers of which the first is kept at a temperature of from 120° to 125°C, the second at a temperature of from 75° to 80°C and the third at ambient temperature. The condensate from the first condenser is supplied to a column for refining distillation, the distillate from the second condenser is returned to the final dehydration stage and the remaining vapors from the third condenser are returned to the water scrubber of the phthalic anhydride plant.

The 534 parts of distillate from the first condenser is processed by refining distillation and 505 parts of pure maleic anhydride is obtained in the lateral discharge of the distillation column having thirty-five trays. This is equivalent to a yield of 85% based on the maleic acid fed in.

We claim:

1. In a process for recovering maleic anhydride formed in the production of phthalic anhydride by catalytic oxidation of o-xylene with air wherein the scrubbing of offgas with water produces an aqueous solution containing up to 40% by weight of maleic acid as well as other oxidation products, the improvement which comprises recovering maleic anhydride from said aqueous solution by:
   a. evaporating water from the aqueous solution in at least one stage at a temperature of from 40°C to 150°C and a pressure of from 50 to 760 mm to give a concentrate containing less than 10% by weight of water, and condensing the aqueous vapors;
   b. heating the concentrate in a film evaporator at a temperature of from 120° to 180°C and a pressure of from 100 to 600 mm;
   c. collecting the condensate obtained by cooling the vapors from said film evaporator to a temperature of from 110° to 140°C, and condensing the aqueous vapors separately at a lower temperature;
   d. distilling said condensate collected at 110° to 140°C through a distillation column to produce pure maleic anhydride;
   e. returning the combined aqueous condensates to the offgas scrubber; and
   f. removing non-volatile impurities as a residue from the film evaporator.

2. A process as set forth in claim 1 wherein the aqueous maleic acid solution is concentrated to a water content of less than 10% by evaporation at a temperature of from 60° to 140°C and a pressure of from 100 to 600 mm, and wherein the concentrate is heated in said film evaporator at a temperature of from 125° to 160°C and a pressure of from 150 to 250 mm.

3. A process as set forth in claim 1 wherein said residue from the film evaporator contains a maleic anhydride concentration of from 30 to 70% by weight.

4. A process as set forth in claim 1 wherein said film evaporator is a thin film evaporator.

5. A process as set forth in claim 1 wherein said film evaporator is a falling-film evaporator.

6. A process as set forth in claim 1 wherein the vapors from said film evaporator are passed through three successive condensers of which the first is maintained at from 120° to 125°C, the second at 75° to 80°C, and the third at ambient temperatures and wherein the condensate from the first condenser is supplied to said distillation column, the condensate obtained in the second condenser is returned to said film evaporator, and the condensate from the third condenser is returned to the offgas scrubber.

7. A process as set forth in claim 1 wherein each stage of the evaporation to form said concentrate is carried out in a film evaporator.

* * * * *

UNITED STATES PATENT AND TRADEMARK OFFICE
CERTIFICATE OF CORRECTION

PATENT NO. : 3,965,126

DATED : June 22, 1976

INVENTOR(S) : WIRTH et al

It is certified that error appears in the above–identified patent and that said Letters Patent are hereby corrected as shown below:

In Column 2, Line 39, delete " ... concentration of maleic acid ... " and substitute -- ... concentration of maleic anhydride ... --

Signed and Sealed this

Eleventh Day of January 1977

[SEAL]

Attest:

RUTH C. MASON
Attesting Officer

C. MARSHALL DANN
Commissioner of Patents and Trademarks